(12) United States Patent
Backlund et al.

(10) Patent No.: US 6,187,106 B1
(45) Date of Patent: Feb. 13, 2001

(54) CONTAINED INSTRUMENT CLEANER FOR USE IN A CONTROLLED ENVIRONMENT

(75) Inventors: David D. Backlund, Hanover; Eyvand E. Toensing, Savage, both of MN (US)

(73) Assignee: Seagate Technology LLC, Scotts Valley, CA (US)

(*) Notice: Under 35 U.S.C. 154(b), the term of this patent shall be extended for 0 days.

(21) Appl. No.: 09/387,997

(22) Filed: Sep. 1, 1999

Related U.S. Application Data
(60) Provisional application No. 60/126,389, filed on Mar. 26, 1999.

(51) Int. Cl.[7] ........................................ B08B 5/04
(52) U.S. Cl. .................. 134/21; 15/310; 451/456; 451/541; 451/558
(58) Field of Search .................. 15/301, 310, 311; 134/21; 451/456, 541, 552, 558

(56) References Cited

U.S. PATENT DOCUMENTS

| | | | |
|---|---|---|---|
| 4,245,437 | * 1/1981 | Marton | 451/456 |
| 5,471,706 | * 12/1995 | Wallock et al. | 15/310 X |
| 5,667,434 | * 9/1997 | Prusaitis et al. | 451/552 |
| 5,915,438 | * 6/1999 | Winters et al. | 15/310 X |

* cited by examiner

Primary Examiner—Chris K. Moore
(74) Attorney, Agent, or Firm—Westman, Champlin & Kelly, P.A.

(57) ABSTRACT

A contained instrument cleaner including a housing having an enclosed chamber and an opening sized to insert an instrument. A rigid member having an abrading surface is supported inside the chamber for cleaning debris from an instrument. The device includes a vacuum channel opened to the chamber and coupleable to a vacuum source for removing debris. A method for cleaning an instrument including the steps of inserting an instrument into an enclosed chamber and rubbing the instrument against an abrading member in the enclosed chamber for removing debris. A vacuum is supplied in the enclosed chamber for collecting debris.

20 Claims, 5 Drawing Sheets

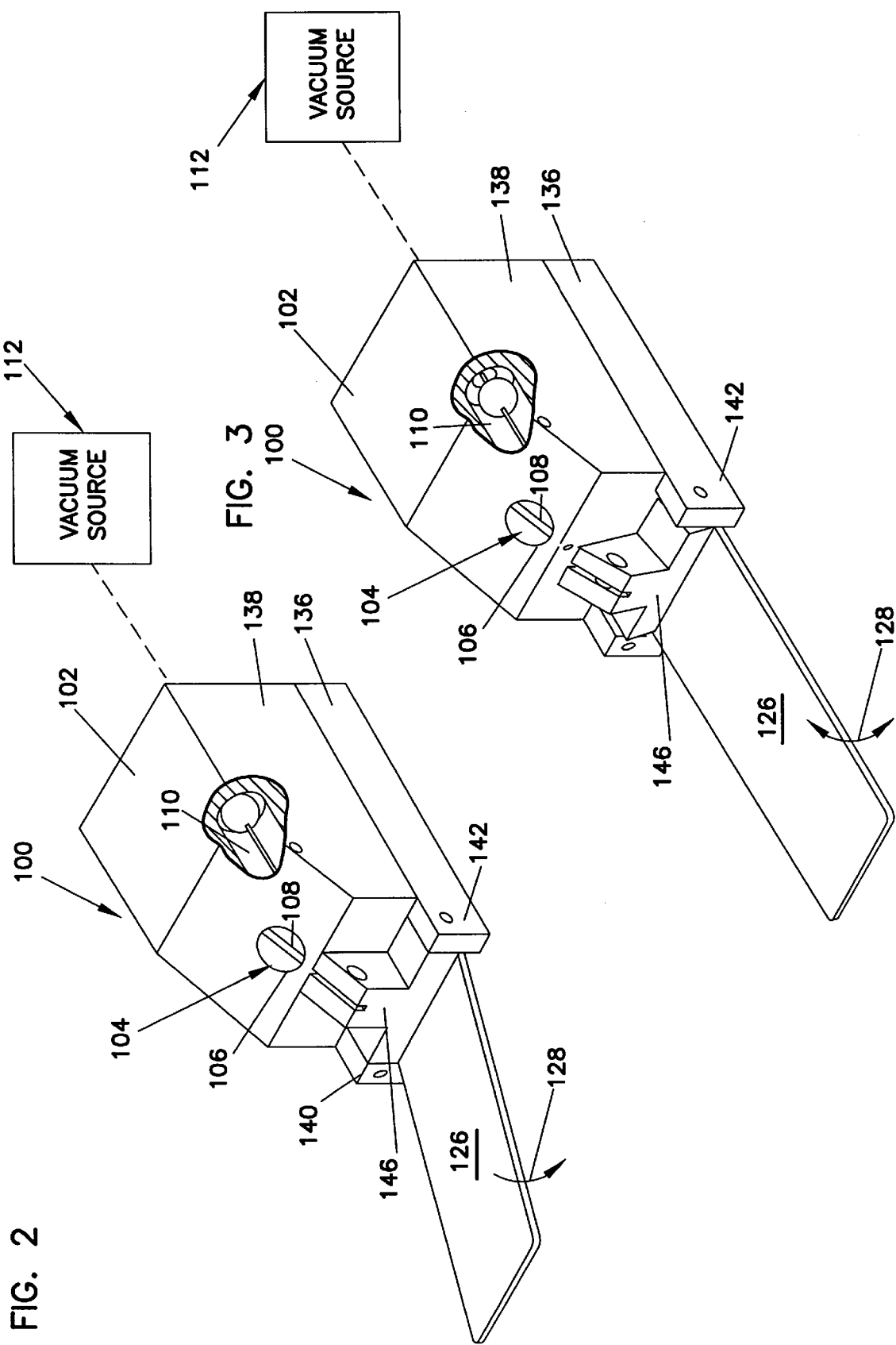

US 6,187,106 B1

CONTAINED INSTRUMENT CLEANER FOR USE IN A CONTROLLED ENVIRONMENT

REFERENCE TO RELATED APPLICATION

The present application claims priority from U.S. provisional application Ser. No. 60/126,389 filed on Mar. 26, 1999.

FIELD OF THE INVENTION

The present invention relates to an apparatus having application for disc drive assembly. In particular, the apparatus has use for removing debris from assembly instruments for clean room application.

BACKGROUND OF THE INVENTION

Disc drives are assembled in clean rooms to limit exposure to debris and particulate which can deposit on drive components degrading drive performance. Instruments, such as tweezers, are used to assemble small components of head gimbal and suspension assemblies of disc drives. Such instruments are periodically cleaned to limit the spread of contaminates to drive components. The cleaning process interrupts disc drive assembly, slowing production. Prior cleaning devices and methods did not contain debris cleaned from instruments. Thus debris cleaned from instruments can resettle on the clean instrument and can contaminate a clean room. The present invention addresses these and other problems, and offers other advantages over the prior art.

SUMMARY OF THE INVENTION

The present invention relates an improved apparatus for cleaning assembly instruments which contains debris to limit recontamination. The present apparatus is adaptable for single handed operation to limit interruption of the assembly process. The apparatus includes a housing having an enclosed chamber and an opening sized to insert an instrument. A rigid member having an abrading surface is supported inside the chamber for removing debris from an instrument. The device includes a vacuum channel opened to the chamber and coupleable to a vacuum source for removing debris cleaned from an instrument to limit recontamination.

BRIEF DESCRIPTION OF THE DRAWINGS

FIG. 2 is a perspective illustration of an embodiment of an apparatus of the present invention in a non-operating mode.

FIG. 3 is a perspective illustration of the apparatus of FIG. 2 in the operating mode.

DETAILED DESCRIPTION OF THE PREFERRED EMBODIMENTS

Figure 1:
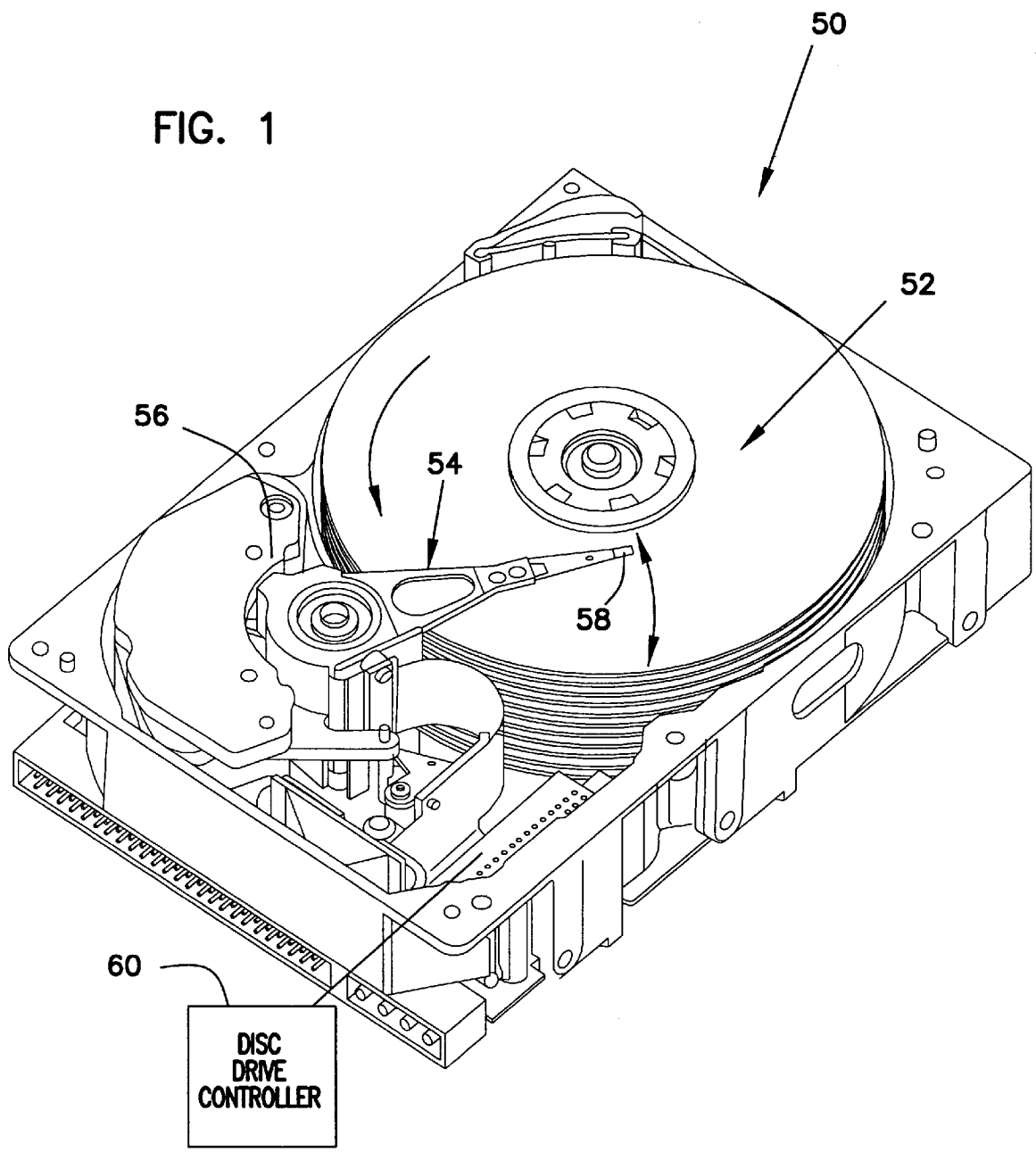
FIG. 1 is a perspective view illustrating a disc drive.

The present invention has application in association with assembling a disc drive 50. Disc drive 50 includes a disc stack 52, an E-block 54 and a voice coil motor 56. E-block 54 supports a plurality of heads 58 for reading or write data relative to a disc surface. Heads can be inductive type heads or magnetoresistive heads. Movement of the E-block 54 is controlled by voice coil motor 56, which is coupled to drive circuitry of the disc drive illustrated by block 60. Operation of the spindle motor (not shown) is also coupled to drive circuitry. Disc drive components are assembled in a clean room. Small components, e.g. heads, are assembled with hand instruments, for example, tweezers. Instruments are periodically cleaned to limit contamination to the drive components or heads.

As previously explained, debris cleaned from instruments can recontaminate a clean room and instruments. FIGS. 2–3 illustrate an embodiment of cleaning apparatus 100 for cleaning assembly instruments for disc drive components which contains and removes debris to limit recontamination for clean room application. As shown in FIGS. 2–3, apparatus 100 includes a housing 102 enclosing an interior chamber 104, an opening 106 through the housing to the interior chamber 104, an abrading member 108 in the chamber 104 (shown schematically) and a vacuum channel 110 opened to the interior chamber 104. As shown schematically in FIGS. 2–3, a vacuum source 112 is coupled to vacuum channel 110 to supply pressure to the interior chamber 104 to expel debris cleaned from an instrument for removal.

Figure 4:
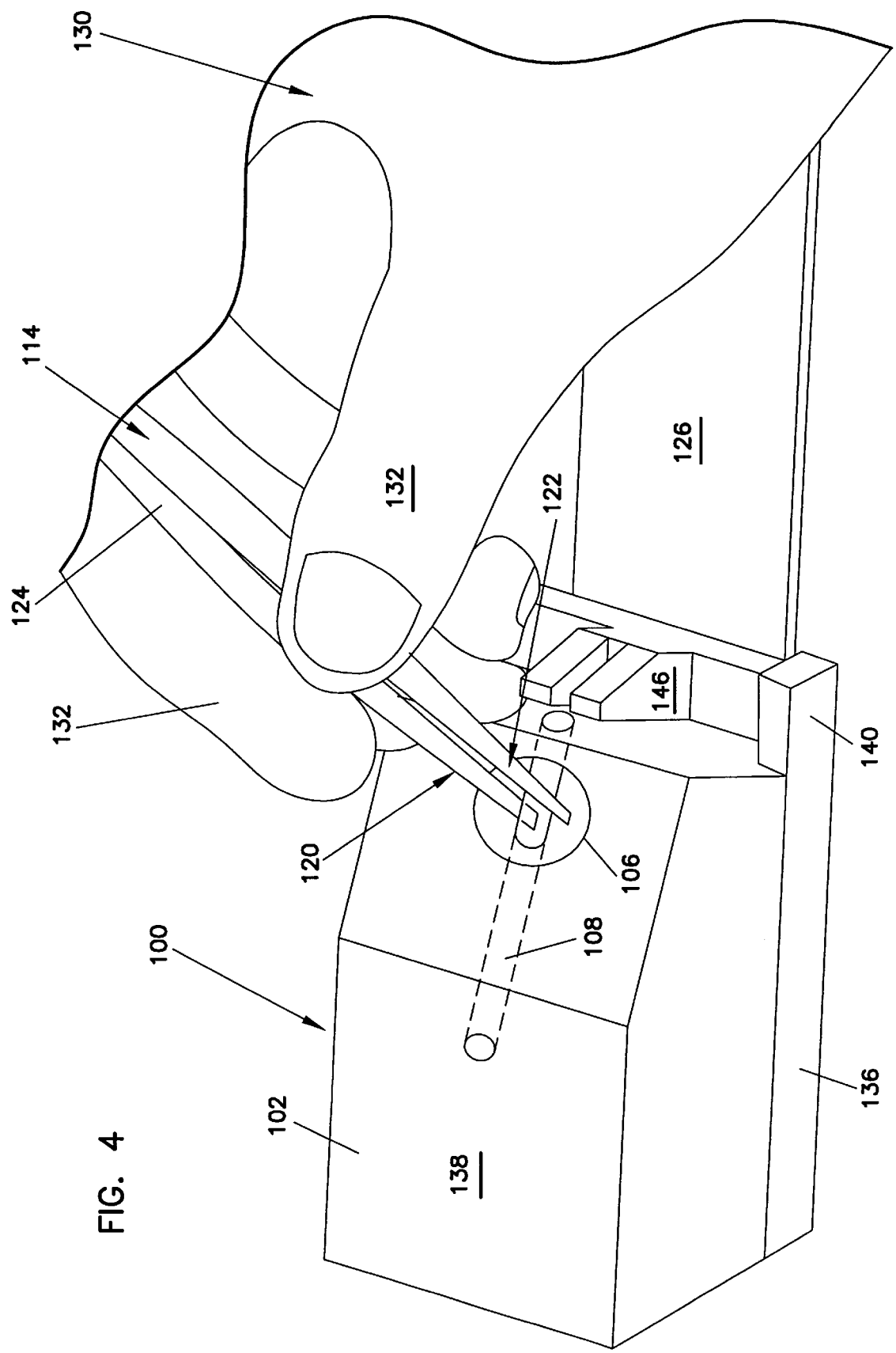
FIG. 4 is a perspective view illustrating single handed operation.

As shown in FIGS. 2–4, opening 106 is sized for insertion of an instrument 114 (shown in FIG. 4). For cleaning operation, instrument 114 is inserted through opening 106 into chamber 104 for contact with abrading member 108. In the embodiment shown, abrading member 108 is formed of an elongated member having a traverse width dimension sized to fit between tweezer legs 120, 122 for cleaning a tweezer instrument 124. Tweezer legs 120, 122 are closed about abrading member 108 to contact abrading member 108. Tweezer legs 120, 122 are rubbed against the abrading member 108 to loosen particles and debris. Abrading member 108 is enclosed in chamber 104 to contain loosen particles and debris and a vacuum is supplied through vacuum channel 110 to remove particles or debris to limit contamination of the operating environment. In the embodiment described, abrading member 108 is a brush having bristles, however, alternate abrading members having different abrading surfaces can be used and application of the invention is not limited to the brush shown.

Apparatus 100 includes an operating mode and a non-operating mode. Apparatus 100 is actuated between the non-operating mode and operating mode to supply vacuum pressure in the operating mode to chamber 104. In FIGS. 2–4, the operating mode is actuated by depressing plate 126 as illustrated by arrow 128. Plate 126 is sized to have sufficient surface area to support a hand palm 130 as shown in FIG. 4. Opening 106 is spaced from plate 126 so that when a user's palm or hand 130 is supported on plate 126 fingers 132 of hand 130 support instrument 114 for insertion through opening 106 for single handed operation. In FIGS. 2–4, opening 106 is spaced from and elevated above plate 126 for single hand operation. Although a particular orientation and design for plate 126 is illustrated, alternate actuator designs can be used and operation is not limited to the exact construction shown.

In FIGS. 2–4, housing 102 includes base 136 and cover 138. Plate 126 is pivotally connected to prongs 140, 142 of base 136 to operate between a raised non-operating position shown in FIG. 2 and a lowered operating position shown in FIG. 3. As shown in exploded FIG. 5, plate 126 is rotationally coupled to base 136 through block 146 which is rotationally connected to base 136 via pin 148 rotationally connected between prongs 140, 142. Plate 126 is normally biased in the non-operating position via spring 150. Spring 150 includes a base portion 152 connected to base 136 and a spring portion 154. Spring portion 154 biases plate 126 connected to block 146 in the raised non-operational position. Abrading member 108 is supported in chamber 104 at opening 106 via set screws 156, 158, although abrading member 108 can be supported by alternate support structures and fasteners.

Figure 5:
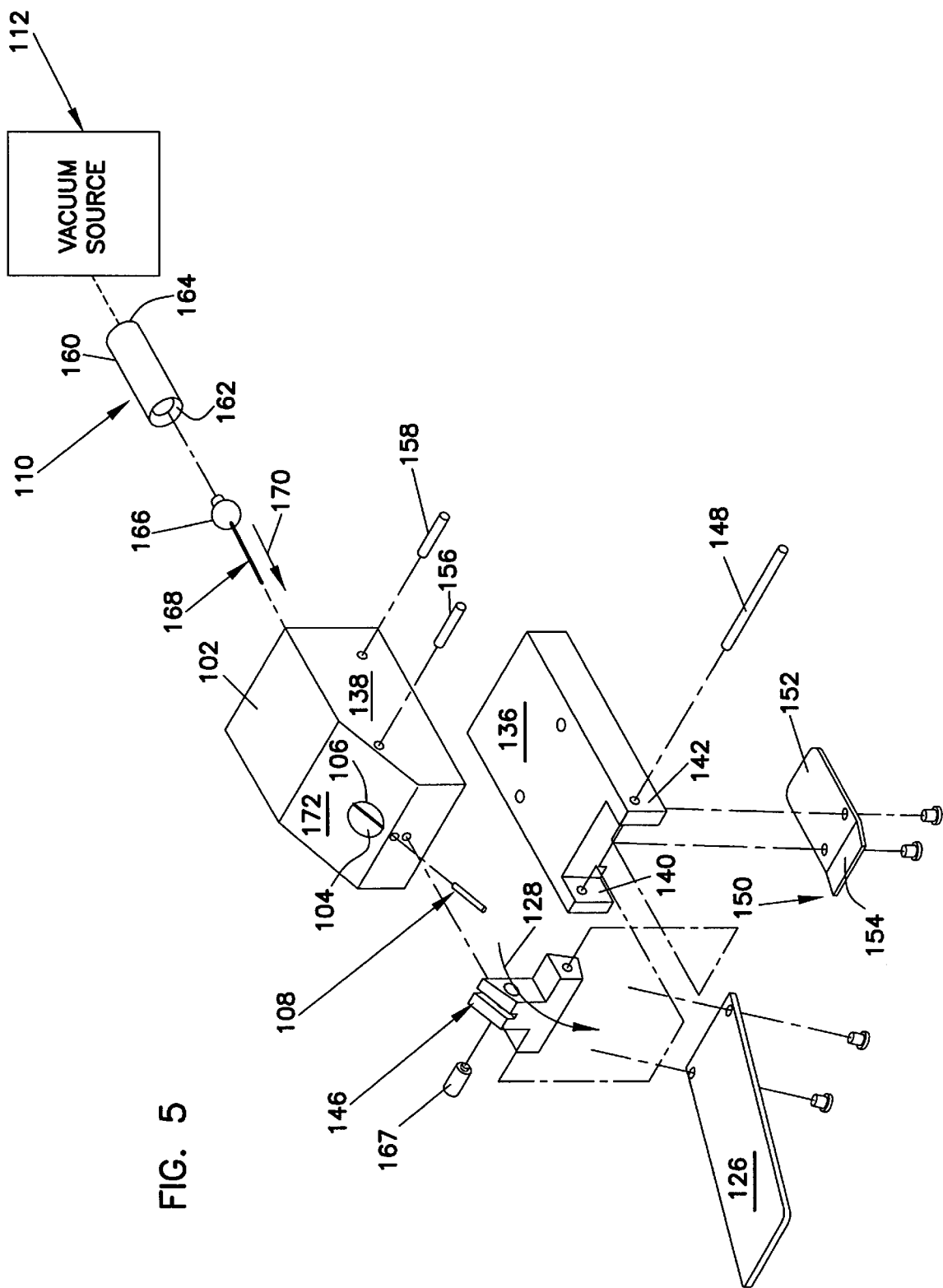
FIG. 5 is an exploded view of the embodiment of the apparatus shown in FIGS. 2–3.

As shown in FIG. 5, vacuum channel 110 is formed through a vacuum tube 160 having an inlet 162 and an outlet 164. Vacuum tube 160 extends through a wall of housing 102 so that inlet 162 is internal in chamber 104 and outlet 164 is external to chamber 104. External outlet 164 is connected to vacuum source 112 for operation. In the embodiment shown, during use vacuum source 112 is "normally on" and inlet 162 includes a closure plug 166 seated in inlet 162 to close vacuum channel to chamber 104 during non-operating periods.

For operation, closure plug 166 is retracted from inlet 162 via operating cord 168 connected to closure plug 166 and block 146 via pin 167. Rotation of block 146 via plate 126 pulls cord 168 to retract closure plug 164 seated against inlet 162 to open inlet 162. In particular, plate 126 is rotated against the spring bias as illustrated by arrow 128 to move cord 168 forward as illustrated by arrow 170 to open inlet 162 to supply vacuum pressure. Although a particular channel closure or actuator is shown, the invention is not limited to a channel plug and other closures and designs, such as solenoid valves, for example, can be employed.

In the embodiment illustrated in FIG. 5, housing 102 includes an inclined face 172 inclined away from plate 126. Opening 106 is on inclined face 172 elevated above plate 126 for inserting an instrument into chamber 104 held by user's finger 132 while the user's palm rests on plate 126. As illustrated in FIG. 4, the inclined position of opening 106 provides easy access to chamber 104 while resting palm on plate 126. Thus, as described, the device illustrated is suited for single handed operation to limit interruption to the assembly process.

Figure 6:
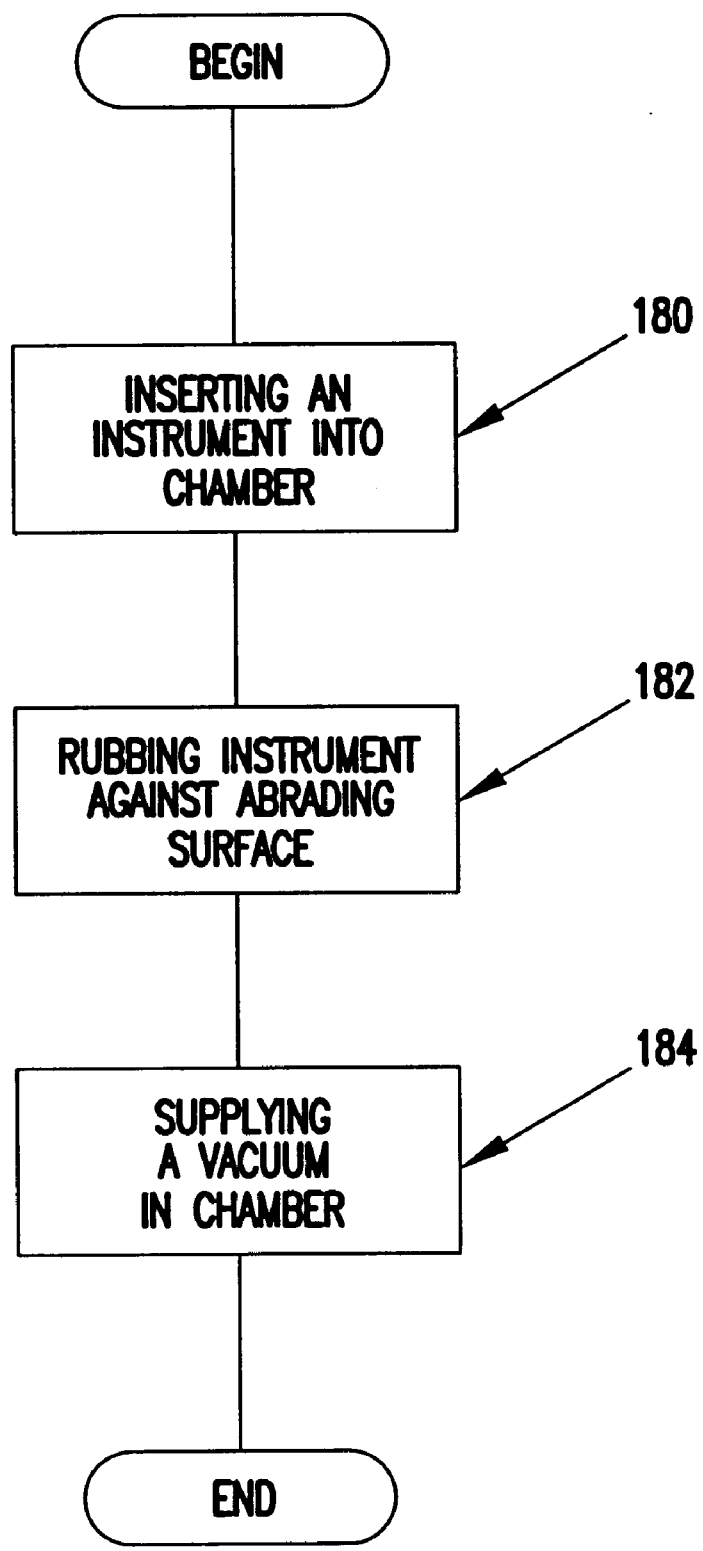
FIG. 6 is a flow chart for cleaning operation of the present invention.

As illustrated in FIG. 6, for use, an instrument 114 is inserted into chamber 104 as illustrated by block 180. The instrument 114 is rubbed against an abrading surface to clean debris and a vacuum is supplied in chamber 104 to remove debris as illustrated in blocks 182, 184.

As described, the present application provides a contained instrument cleaner including a housing 102 having an enclosed chamber 104 and an opening 106 sized to insert an instrument. A rigid member 108 having an abrading surface is supported inside the chamber 104 for removing debris from an instrument 114. The device includes a vacuum channel 110 opened to the chamber 104 and coupleable to a vacuum source 112 for removing debris.

It is to be understood that even though numerous characteristics and advantages of various embodiments of the present invention have been set forth in the foregoing description, together with details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, the particular elements may vary depending on the particular application while maintaining substantially the same functionality without departing from the scope and spirit of the present invention. In addition, although the preferred embodiment described herein is directed to assembly instruments for a disc drive, it will be appreciated by those skilled in the art that the teachings of the present invention can be applied to other instruments for clean room assembly without departing from the scope and spirit of the present invention.

What is claimed is:

1. An apparatus for removing debris from an instrument comprising:
   a housing having an enclosed chamber;
   a rigid abrading member having an abrading surface supported inside the chamber;
   an opening sized for inserting the instrument into the chamber; and
   a vacuum channel opened to the chamber and coupleable to a vacuum source for removing debris.

2. The apparatus of claim 1 and comprising
   a vacuum source coupled to the vacuum channel.

3. The apparatus of claim 1 including;
   an actuator for activating the apparatus in an operating mode, to supply vacuum pressure to the chamber to remove debris.

4. The apparatus of claim 3 wherein the actuator includes a plate to operate the apparatus in the operating mode.

5. The apparatus of claim 4 wherein the plate is sized to support a hand for actuation.

6. The apparatus of claim 5 wherein the plate and the opening are spaced for single handed operation of the apparatus in the operating mode.

7. The apparatus of claim 4 wherein the housing includes a base and the plate is rotationally coupled to the base.

8. The apparatus of claim 4 wherein the plate is normally spring biased in a raised non-operating position.

9. The apparatus of claim 3 including
   a vacuum channel closure operable between a retracted position and a sealing position, in the retracted position the vacuum channel closure being spaced from the vacuum channel to supply vacuum pressure to remove debris and in the sealing position, the vacuum channel closure sealing the chamber.

10. The apparatus of claim 9 wherein the vacuum channel is coupled to a "normally on" vacuum source.

11. The apparatus of claim 9 wherein the actuator includes a plate and the plate is coupled to the vacuum channel closure by an operating cord.

12. The apparatus of claim 1 wherein the opening is on an inclined surface of the housing.

13. The apparatus of claim 1 wherein the rigid abrading member is a brush having a bristle abrading surface.

14. The apparatus of claim 1 wherein the abrading member is elongated having a transverse width dimension sized for insertion between legs of a tweezer.

15. The apparatus of claim 1 wherein the abrading member is formed of an elongated member having an elongated extent supported along an incline in alignment with the opening.

16. An apparatus for removing debris comprising:
   a housing having an enclosed chamber and an instrument opening opening into the chamber; and
   means in said chamber for cleaning debris from the instrument and for removing debris from said chamber for collection.

17. A method for cleaning an instrument comprising the steps of:
   (a) providing an apparatus including an enclosed chamber having an abrading member supported therein;

(b) inserting an instrument through an opening into the chamber;

(c) rubbing the instrument against the abrading member for removing debris; and (d) supplying a vacuum in the chamber for removing debris for collection.

18. The method of claim 17 comprising:

(e) single handedly inserting the instrument through the opening into the chamber and actuating a vacuum source for removing debris for collection.

19. The method of claim 17 comprising:

(e) single handedly depressing a plate to supply a vacuum to the chamber.

20. The method of claim 17 comprising:

(e) inserting tweezers through the opening into the chamber; and (f) aligning the abrading member between first and second tweezer legs.

* * * * *